United States Patent [19]

Crawford et al.

[11] Patent Number: 5,985,665
[45] Date of Patent: Nov. 16, 1999

[54] BIOCHEMICAL ANALYSIS OF ANTIOXIDANT FUNCTION OF LYMPHOCYTES IN CULTURE

[75] Inventors: J. Fred Crawford, Houston, Tex.; Luke Bucci, West Valley City, Utah

[73] Assignee: Research Development Foundation, Carson City, Nev.

[21] Appl. No.: 08/665,941

[22] Filed: Jun. 19, 1996

[51] Int. Cl.$^6$ ............... C12N 5/00; A01N 1/02; C12Q 1/02; G01N 1/00
[52] U.S. Cl. ............... 435/404; 435/4; 435/14; 435/29; 435/372; 435/375; 435/387; 435/405; 435/406; 435/2
[58] Field of Search ............... 435/404, 405, 435/372, 375, 40.5, 2, 4, 14, 29, 387, 406

[56] References Cited

U.S. PATENT DOCUMENTS 4,499,064  2/1985  Shive ............... 435/14
4,927,762  5/1990  Darfler ............... 435/387

*Primary Examiner*—Leon B. Lankford, Jr.
*Assistant Examiner*—Christopher R. Tate
*Attorney, Agent, or Firm*—Benjamin Aaron Adler

[57] ABSTRACT

The present invention provides a cell culture medium useful for a biochemical analysis of antioxidant function in human lymphocytes, said medium comprising, a buffered, serum-free solution containing the following ingredients: a carbohydrate selected from the group consisting of glucose and a compound biologically capable of producing glucose in the cells, a biologically usable form of pantothenic acid, choline or a biological usable form of a substance capable of producing choline in the cells, inorganic ions comprising chloride, phosphate, calcium, magnesium, potassium, sodium, and iron in a biologically utilizable form, cumene hydroperoxide, deionized water, and a mitogen in an amount effective to stimulate the lymphocytes being assayed; said buffered, serum-free solution having a pH from about 6.8 to 7.6, said cell culture medium characterized by being effective to determine nutritional deficiencies, inadequacies, and imbalances and to biochemically analyze antioxidant function of the lymphocytes. Also provided is a method of biochemically analyzing cellular antioxidant function in an individual comprising the steps of: inoculating the cell culture medium of the present invention with lymphocytes from said individual; incubating the inoculated cell culture medium; and comparing the response of the lymphocytes with an average response of lymphocytes from a control group of individuals.

7 Claims, 1 Drawing Sheet

BIOCHEMICAL ANALYSIS OF ANTIOXIDANT FUNCTION OF LYMPHOCYTES IN CULTURE

BACKGROUND OF THE INVENTION

1. Field of the Invention

The present invention relates generally to the fields of nutrition and physiological chemistry. More specifically, the present invention relates to a novel biochemical analysis of antioxidant function.

2. Description of the Related Art

An individual's cells are constantly subjected to highly reactive and unstable molecules called free radicals which cause oxidative stress. These hostile molecules are a normal byproduct of life and are produced by metabolism of oxygen, i.e., cellular respiration, immune system cells (killing of foreign materials) and by numerous enzyme reactions essential for metabolism. Environmental sources of free radicals include smoke, ionizing radiation, air pollution, chemicals (carcinogens, many petrochemicals, biocides, dyes, solvents, cytostatic drugs, etc.), toxic heavy metals and oxidized (rancid) fats. Some of the most common free radicals are superoxide, hydroxyl, singlet oxygen, and peroxides. Certain valences of iron and copper can catalyze formation of free radicals, which although short-lived, promote a chain reaction of radical formation, followed by a wake of altered, damaged biological molecules.

Free radicals are toxic to living organisms, causing structural damage to all biological molecules. Molecular damage may translate into alteration of genetic codes, disruption of cell membrane integrity, neurological disorders, endocrine imbalances, increased allergies, vascular endothelial destruction, and joint degradation and inflammation.

Protection from the deleterious effects of free radicals is found in a diverse range of molecules termed antioxidants. Free radicals, and their chain byproducts can be neutralized and converted to less harmful products by antioxidants. Antioxidants may be enzymes (such as superoxide dismutase, catalase, glutathione peroxidase), essential nutrients (such as beta carotene, vitamins C and E, selenium and cysteine) or a wide variety of endogenous (such as glutathione) or dietary compounds (such as the bioflavanoids). Thus, the human body has different quenchers of free radicals.

Research in humans has indicated that deficient intakes of nutrient antioxidants are associated with higher risks of cancer, cardiovascular disease, arthritis, cataracts, etc. Also, higher intake of nutrient antioxidants are associated, with lower incidence of chronic degenerative diseases. Encouraging studies indicate that intervention with antioxidant nutrient supplements may have therapeutic benefit in humans.

Laboratory analysis of antioxidant status has not become routine for a variety of reasons. Free radicals are extremely fleeting and generally not amenable to direct measurement. By products of free radical damage can be measured as malondialdehyde (MDA), thiobarbituric acid-reactive substances (TBARS) or lipid peroxides in serum or urine. These tests are indicators of oxidative stress but only reflect damage to certain types of biomolecules (mostly polyunsaturated lipids and nucleic acids). Measurement of antioxidant nutrient levels in serum or cells, and activities of antioxidant enzymes in cells can identify deficient levels of specific components, but gives little information on the interaction and net function of antioxidants. Other tests for oxidative stress are available in research settings but are unsuitable for routine clinical laboratory use because of their complexity and cost.

The prior art is deficient in the lack of simple cost-effective means of biochemical analyzing antioxidant function in a human. The present invention fulfills this long-standing need and desire in the art.

SUMMARY OF THE INVENTION

In one embodiment of the present invention, there is provided a a cell cuture medium useful for a biochemical analysis of antioxidant function in human lymphocytes, said medium comprising, a buffered, serum-free solution containing the following ingredients: a carbohydrate selected from the group consisting of glucose and a compound biologically capable of producing glucose in the cells, a biologically usable form of pantothenic acid, choline or a biological usable form of a substance capable of producing choline in the cells, inorganic ions comprising chloride, phosphate, calcium, magnesium, potassium, sodium, and iron in a biologically utilizable form, cumene hydroperoxide, deionized water, and a mitogen in an amount effective to stimulate the lymphocytes being assayed; said buffered, serum-free solution having a pH from about 6.8 to 7.6, said cell culture medium characterized by being effective to determine nutritional deficiencies, inadequacies, and imbalances and to biochemically analyze antioxidant function of the lymphocytes.

In another embodiment of the present invention, there is provided a method of biochemically analyzing cellular antioxidant function in an individual comprising the steps of: inoculating the cell culture medium of the present invention with lymphocytes from said individual; incubating the inoculated cell culture medium; and comparing the response of the lymphocytes with an average response of lymphocytes from a control group of individuals.

In yet another embodiment of the present invention, there is provided a method of determining abnormal quantitative nutritional requirements for specific required nutrients in an individual comprising the steps of: inoculating the cell culture medium of the present invention with lymphocytes from said individual, said culture medium having limiting concentrations of the nutrient being tested; incubating the inoculated cell culture medium;

and comparing the response of the lymphocytes with an average response of lymphocytes from a control group of individuals. In yet another embodiment of the present invention, there is provided a method of identifying nutritional factors or biochemical intermediates which overcome detrimental effects of nutrients, biochemical intermediates or their products, and other blood components including drugs in an individual sensitive to such detrimental effects comprising the steps of: inoculating the cell culture medium of the present invention containing at least one of the nutrients, biochemical intermediates or products or other blood components including drugs at a concentration having a detrimental effect on the cell response; incubating the inoculated cell medium; and comparing the response with that in the same medium supplemented with a source of the substance suspected to affect the detrimental effect of the nutrient, biochemical intermediate or its product or other blood component including the drug being tested.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
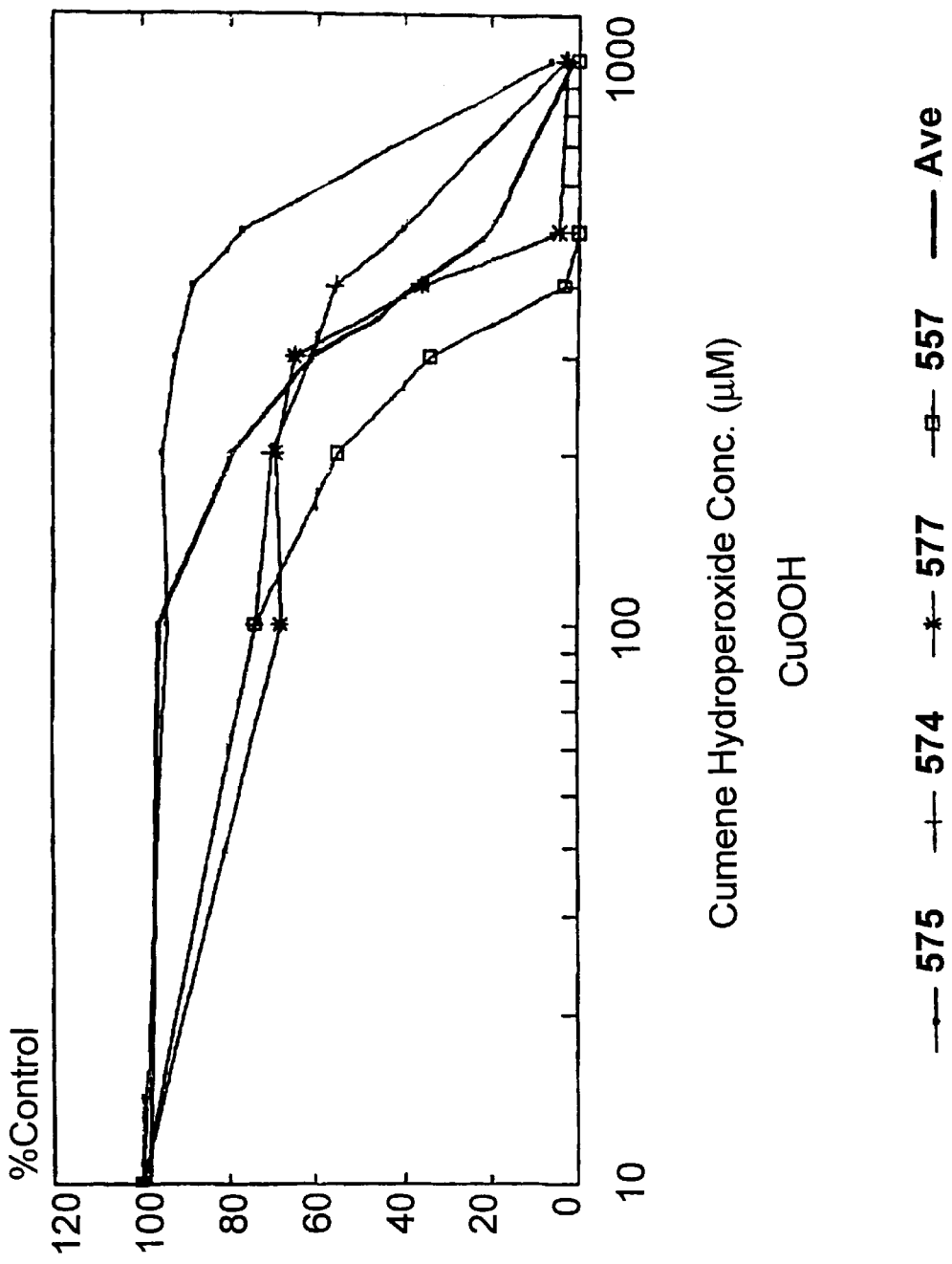
FIG. 1 shows the dose response curve of cumene hydroperoxide from a reference range population.

The present invention is directed to blood tests which assess intracellular vitamin deficiencies and total antioxidant function providing a novel biochemical analysis of an individual's cells. Such an analysis reflects how well nutrients and antioxidant systems are actually functioning within an individual's peripheral lymphocytes. Where determining intracellular vitamin status was previously impossible, the methodology of the present invention allows deficiencies to be precisely detected before they contribute to clinical problems.

Until the development of the present invention, vitamin testing was based on clinical observation and measurements of static levels in serum, urine or hair, along with certain enzyme or protein markers. Such tests indicate short-term static levels, and do not assess the many complicated metabolic pathways in which these compounds participate as enzymatic cofactors. Thus, other methodologies frequently report results which are functionally inaccurate and are, therefore, clinically useless.

Instead of measuring static levels, the method of the present invention analyzes how vitamins, minerals, amino acids and antioxidant systems are actually functioning within an individual's white cells. Unlike other methodologies, even those claiming to be functional, the method of the present invention utilizes metabolically active peripheral lymphocytes and measures DNA synthesis (cell growth) to identify functional intracellular deficiencies that limit mitogenic responses. Thus, the method of the present invention provides test results which reflect total metabolic function rather than serum level tests, or tests utilizing isolated biochemical pathways.

Lymphocytes offer distinct advantages, because they: (1) are host to the cell-mediated immune system and are easily stimulated to grow (mitogenesis); (2) reflect time-averaged, long-term nutrient status (the life of a lymphocyte is about six months); (3) possess metabolic pathways common to other cells, contain a nucleus which permits rapid DNA synthesis and cell growth and are easily collected by standard venipuncture.

The method of the present invention is the only blood test that identifies functional deficiencies intracellularly by measuring the DNA synthesis (cell growth) in each patient's lymphocytes using a chemically-defined culture media, free of serum or protein. The control media contains the minimal amount of each essential nutrient needed to support optimal lymphocyte growth, or mitogenic response. The functional status of 19 different vitamins, minerals and amino acids involved in cell metabolism is directly determined by making lymphocyte growth dependent on the manipulation of individual nutrients in the media and measuring the resulting DNA synthesis. More importantly, the method of the present invention provides a total antioxidant function test which assesses the overall ability of cells to resist damage caused by free radicals and other forms of oxidative stress. Because of the considerable number of cellular antioxidants—with extensive interactions, redundancies, repair and recharging capabilities—measuring total function is the most accurate and clinically iseful way to assess overall antioxidant status. By using each patient's living, metabolically active lymphocytes, the method of the present invention provides a more accurate and clinically useful analysis of vitamin and mineral status than any prior art laboratory test.

By measuring lymphocyte growth to assess functional adequacy, the method of the present invention reflects the unique requirements of each patient, which vary widely. Therefore, repletion can be tailored to the specific biochemical requirements of the individual rather than the "average" patient as determined by so-called norms.

According to published studies, 70% of the U.S. population are at risk for long-term vitamin and mineral deficiencies. These deficiencies can adversely affect the body's efficient functioning and its ability to resist disease. Scientific evidence shows that correcting vitamin deficiencies enhances immunocompetence and aids in the prevention or correction of chronic degenerative health conditions. Studies also show that significant intracellular functional deficiencies occur in over 40% of patients already taking vitamins. Furthermore, Recommended Dietary Allowance (RDAs) are not appropriate guidelines for assessing individual vitamin and mineral requirements.

Many individuals can benefit from the present invention. The correction of vitamin deficiencies is essential for healthy patients concerned with maintaining wellness. A baseline test for these patients is vital. A growing body of medical research is continually documenting numerous disease processes that are associated with vitamin deficiencies. These studies demonstrate the preventive and therapeutic benefits of optimal vitamin, mineral, amino acid and antioxidant status—from contributing to the prevention of heart disease and various forms of cancer, to stimulating immune system functions and slowing of age-related declines in physiological functions. In addition, health conditions such as alcoholism and substance abuse, arthritis, chronic fatigue, diabetes, HIV/AIDS and other immune disorders, macular degeneration, malaise and fatique, multiple sclerosis, neural tube defects, obesity, osteoporosis and pregnancy can be affected, directly or indirectly, by vitamin and mineral deficiencies, and repletion has been shown to contribute to the arrest or prevention of these chronic health conditions.

Although the presently preferred embodiments of the present invention are described in detail below, various basic components of the assay of the present invention, e.g., solutions, culture media, salts and other components are described in U.S. Pat. No. 4,499,064.

The present invention is directed to a cell cuture medium useful for a biochemical analysis of antioxidant function in human lymphocytes, said medium comprising, a buffered, serum-free solution containing the following ingredients: a carbohydrate selected from the group consisting of glucose and a compound biologically capable of producing glucose in the cells, a biologically usable form of pantothenic acid, choline or a biological usable form of a substance capable of producing choline in the cells, inorganic ions comprising chloride, phosphate, calcium, magnesium, potassium, sodium, and iron in a biologically utilizable form, cumene hydroperoxide, deionized water, and a mitogen in an amount effective to stimulate the lymphocytes being assayed; said buffered, serum-free solution having a pH from about 6.8 to 7.6, said cell culture medium characterized by being effective to determine nutritional deficiencies, inadequacies, and imbalances and to biochemically analyze antioxidant function of the lymphocytes.

In one embodiment, the cell cuture medium is supplemented with a nutrient supplement selected from the group consisting of biological utilizable forms of amino acids and vitamins, the nutrient being tested for being omitted from or being present in limiting or inhibitory amounts in the nutrient supplement. In this case, the vitamins are selected from the group consisting of biotin, folinic acid or a biologically usable form of folic acid, nicotinamide or nicotinic acid, riboflavin, thiamin, vitamin $B_6$, and vitamin $B_{12}$, and compounds capable of producing them in the cells; and wherein said amino acids or the compounds biologically capable of producing the amino acids comprise L-arginine, L-cysteine, L-glutamine, glycine, L-histidine, L-isoleucine, L-leucine, L-lysine, L-methionine, L-phenylalanine, L-serine, L-threonine, L-tryptophan, L-tyrosine, and L-valine, the amino acids being present as a group, each in an amount not exceeding inhibitory concentrations.

Generally, the cell cuture medium of the present invention contains a concentration of cumene hydroperoxide which permits an accurate biochemical analysis of antioxidant function to be made. Preferably, the concentration of cumene hydroperoxide in the cell cuture medium is from about 50 $\mu$M to about 500 $\mu$M.

In another embodiment, the cell culture medium of the present invention is supplemented at concentrations eliciting approximately a maximal response with one or more stimulatory nutrients selected from the goup consisting of pyruvate, adenine, and inositol or compounds capable of producing them within the cells. Generally, each amino acid of the amino acid supplement being present in about the minimum concentration effective for a maximal response of the cells except the amino acid being tested. Further, when the medium is free of either or both serine and glycine, and in which an effective concentration for cell response of either or both vitamin $B_6$ and a utilizable form of folic acid are included in the culture medium. In another embodiment, when the medium is free of one of pantothenic acid and choline, the cell culture in said medium being effective to determine nutritional deficiencies and abnormal requirements when supplemented with response limiting amounts of pantothenic acid and choline of which the culture medium is free.

The present invention is also directed to a method of determining abnormal quantitative nutritional requirements for specific required nutrients in an individual comprising the steps of: inoculating the cell culture medium of claim 1 with lymphocytes from said individual, said culture medium having limiting concentrations of the nutrient being tested; incubating the inoculated cell culture medium; and comparing the response of the lymphocytes with an average response of lymphocytes from a control group of individuals.

The present invention is further directed to a method of identifying nutritional factors or biochemical intermediates which overcome detrimental effects of nutrients, biochemical intermediates or their products, and other blood components including drugs in an individual sensitive to such detrimental effects comprising the steps of: inoculating the cell culture medium of claim 1 containing at least one of the nutrients, biochemical intermediates or products or other blood components including drugs at a concentration having a detrimental effect on the cell response; incubating the inoculated cell medium; and comparing the response with that in the same medium supplemented with a source of the substance suspected to affect the detrimental effect of the nutrient, biochemical intermediate or its product or other blood component including the drug being tested.

The present invention provides a method of biochemically analyzing cellular antioxidant function in an individual comprising the steps of: inoculating the cell culture medium of claim 1 with lymphocytes from said individual; incubating the inoculated cell culture medium; and comparing the response of the lymphocytes with an average response of lymphocytes from a control group of individuals. Various aspects of this embodiment are described in detail infra.

The following examples are given for the purpose of illustrating various embodiments of the invention and are not meant to limit the present invention in any fashion.

EXAMPLE 1
Drawing Patient's Blood

Two 10 ml whole blood specimens preserved with acid-citrate-dextrose are required for the method of the present invention. No fasting is required. All that's required are blood drawing supplies. The assay of the present invention may then be performed or the patient's blood should be shipped to a suitable laboratory at room temperature. No centrifuging of the blood was required. Comprehensive test results provided a sound, scientifically-based analysis of the patient's deficiencies.

EXAMPLE 2
Sample Processing: Cell Isolation

All procedures are conducted using sterile techniques under a laminar flow hood to insure sample sterility. Each patient's blood samples are assigned on Accession number upon receipt at the laboratory. This accession number is used as the sample number to enable tracking throughout processing, data collection and data analysis steps. Every test tube, centrifuge tube, microtiter plate and data printout involved with processing the patients sample is labeled with this sample (accession) number.

Each patient sample consists of (2) two Acid-Citrate-Dextrose (yellow top) vaccutainer type tubes, each containing 8 ml of whole blood. After being assigned an accession (sample) number, the whole blood was mixed by inverting 6 times. The two tubes of whole blood were combined into a 50 ml disposable centrifuge tube.

A 500 $\mu$l aliquot was aseptically removed from each sample and placed in a 12×17 mm tube. This aliquot was used to perform a whole blood cell count on the Coulter Cell Counter, Model T540. The whole blood cell count printout from the Coulter was labeled with the accession number and attached to the Worksheet for that patient.

Two (2) Ficoll gradient tubes were prepared for each sample by the addition of 5.0 ml of Histopaque 1077 (Ficoll/Sodium Diatrizoate, Sigma Chemicals, St. Louis, Mo.) to each 15 ml conical centrifuge tube. Using a 10 ml pipette and an electric pipette aide, 8 ml of whole blood is slowly layered onto each of the Ficoll gradient tubes. The Ficoll gradient tubes were capped and centrifuged at 2160 RPM for 20 minutes.

After centrifugation was complete, the gradient tubes were carefully removed from the centrifuge to avoid disrupting the gradient. The buffy coat (containing the lymphocytes) found at the interface of the middle Ficoll layer was transferred using a 5 ml pipette into a 15 ml disposable conical centrifuge tube. The buffy coat was combined with phosphate buffered saline-0.72% glucose solution (PBS-G) to a final volume of 12 ml. The tube was capped and inverted 6 times to mix the buffy coat and the PBS-G.

The tubes containing buffy coat and PBS-G were centrifuged at 2160 RPM for 5 minutes. After centrifugation the supernatant was aspirated from the cell pellet and discarded. The cell pellet was resuspended into 12 ml of PBS-G, inverted 6 times to insure adequate dispersal of the cell pellet. The sample was then centrifuged again as described above.

After the second centrifugation, the supernatant was aspirated and discarded. The cell pellet was resuspended in 6.0 ml of PBS-G. The cell pellet was disrupted and mixed with the PBS-G using a 5 ml pipette attached to an electric pipet aide. After a homogeneous cell suspension has been attained, a 200 μl aliquot of the suspension was transferred into a 12×75 mm tube. This aliquot was used to perform the initial cell suspension (ICS) count with the Coulter Cell Counter Model T540.

The printout from this aliquot was labeled with the sample number and attached to the Worksheet. If the lymphocyte number was between 3.9 and 1.2 thousand cells per cubic millimeter (THSD/mm$^3$) the sample is ready for plate inoculation. The volume of cell suspension to be added is found in the TABLE III. If the lymphocyte number was greater than 3.9 THSD/mm$^3$ the sample must be rediluted. If however, the lymphocyte number was less than 1.2 THSD/mm$^3$ the sample was rejected.

The amount of additional PBS-G that is required for proper redilution was determined using the following calculations:

$$C_1, V_1 = C_2 V_2 \quad C = \text{Lymphocyte Concentration (THSD/mm}^3)$$

$$V = \text{Volume}$$

Where $C_2$=3.0 THSD/mm$^3$, this was the desired lymphocyte concentration of the final cell suspension. For example, when the initial Cell Suspension Count from 6.0 ml=(LY# of 5.6 THSD/mm$^3$ $$C_1, V_1 = C_2 V_2 \quad (5.6)(6.0 \text{ ml}) = (3.0)(X)$$

$$X = 11.2 \text{ ml final volume.}$$

An appropriate volume of PBS-G was added to resuspend cells for a final volume of 11.2 ml. In this example, 5.2 ml would be added to the original 6.0 ml for a final volume 11.2 ml. The required volume of PBS-G was added to the (ICS) to make the Final Cell Suspension (FCS). The LY# count and PBS-G volume were recorded on the Spectrox Test Worksheet.

After redilution, a 200 μl aliquot of the rediluted cell suspension was transferred into a new 12×75 mm tube and a cell count performed as described. The rediluted cell suspension printout (Final Cell Suspension LY#) was attached to work sheet and the inoculation volume recorded.

EXAMPLE 3

Plate Inoculation

The final cell suspension was placed into a sterile trough. Place a microtiter plate containing media inside the laminar flow hood. Using a 12-channel manual micropipettor equipped with sterile 0–50 μl barrier tips, the specified amount (according to TABLE I) of final cell suspension was dispensed to each well in Row "H" of the plate.

TABLE I

The following volumes are used for plate inoculation based on the listed final cell suspension Lymphocyte number (LY#).

| Final Cell Suspension LY# | Adjusted Volume For Inoculation |
| --- | --- |
| 3.9–.37 | 8.0 μl |
| 3.6 | 8.5 μl |
| 2.5–3.5 | 10.0 μl |
| 2.4 | 12.5 μl |
| 2.3 | 13.0 μl |
| 2.2 | 14.0 μl |
| 2.1 | 14.5 μl |
| 2.0 | 15.0 μl |
| 1.9 | 16.0 μl |
| 1.8 | 17.0 μl |
| 1.7 | 18.0 μl |
| 1.6 | 19.0 μl |
| 1.5 | 20.0 μl |
| 1.4 | 21.5 μl |
| 1.3 | 23.0 μl |
| <=1.2 | 25.0 μl |

After addition of the cells to the media, cumene hydroperoxide (CuOOH) solutions were added to Row "H" in the following manner:

(1) Columns 1, 2, 3 received 10 μl of 100 μM CuOOH;

(2) Columns 4, 5, 6 received 10 μl of 200 μM CuOOH;

(3) Columns 7, 8, 9 received 10 μl of 300 μM CuOOH; and (4) Columns 10,11,12 received 10 μl of 400 μM CuOOH.

After addition of CuOOH to microtiter plate, the cover was placed on the plate which was placed into a $CO_2$ incubator and maintained at 37° C. for 96 hours.

EXAMPLE 4

Labeling

All labeling procedures were performed in the Radioisotope Room. The tritiated thymidine ($H^3$-TdR) working solution was removed from the refrigerator and warmed to 37° C. in a water bath. After 96 hours, the microtiter plates was removed from the incubator. The $H^3$-TdR working solution was placed in a sterile trough and a 12-channel manual micropipettor equipped with 0–50 μl sterile barrier tips were used to dispense 10 μl of the $H^3$-TdR working solution into each well in row "H" of the microtiter plate. The plate was returned to the 37° C. incubator for 24 hours. The date and initials of the technician performing the labeling was recorded on the sample log sheet.

EXAMPLE 5

Harvesting

All harvesting procedures were performed in the Radioisotope Room. A single glass fiber filter mat (Packard Part # 6005416) was labeled with the sample number using a number 2 pencil. The vacuum pump was turned on and the drying oven set at 100° C. The distilled water carboy attached to the harvester was filled. The microtiter plates wer removed from the incubator 24 hours after the addition of $H^3$-TdR. The date and initials of the technician performing harvesting was recorded on the sample log sheet.

With the Cell Harvester (Packard Model # C9619) in the open position, O-Rings exposed, the glass fiber filter mat was placed onto the harvester with the rough side touching the O-Rings. The cell harvester was closed and the filter mat was wet with distilled water from the rinse tray. The harvester was left on vacuum cycle (VAC). The lid was removed from microtiter plate and the plate was placed under harvester probe tips. The plate was slowly raised onto harvester probes, until the tips of the probe touch the bottom of the plate. With the media aspirated, the bottom of the wells was scrubbed with the probe tips by moving the microtiter plates slowly in a circular motion. Scrubbing was continued for 10 seconds. With the microtiter plate in contract with the harvester probe tips, scrubbing was continued and the "WASH" button was pressed for 10 seconds. Liquid was aspirated from wells and the steps above were repeated. The plate was removed, the rinse tray filled with methanol, the tray raised, the methanol aspirated and the tray lowered.

The harvester was opened, with the filter mat adhering to the upper section and continued to operate on VAC for 5 seconds. After 5 seconds, the VAC was simultaneously turned off and filter mat was removed from the harvester surface. The filter mat was placed rough side up in drying oven for 10 minutes. The filter mats were removed from the oven and cooled to room temperature.

EXAMPLE 6
Counting Of Radioactivity

All counting procedures were conducted in the Radioisotope Room. The filter mat loaded into counting cassette, rough side up. A collimator (thin stainless steal plate that holds filter mat in place) placed over filter mat. The cassettes loaded into Packard Matrix 9600 Beta Particle Radioactivity Counter. The flow of Q-Gas (1.3% n-butane in helium) started into Matrix 9600. The "START" button was pressed activating the counting protocol which counts total radioactivity in each well for 3 minutes. Each sample count was stored in the hard drive of the Matrix 9600. In addition, a hard copy of the raw radioactivity counts was printed out.

EXAMPLE 7
Data Transformation

Data was downloaded from the Matrix 9600 hard drive onto a 3.5 diskette. The raw data was transformed into a reportable format using a macro executed in Microsoft Excel. This macro subtracts the plate background from each data point, generates an average for the triplicate well values, and presents this value as a percentage of the Plate Control value which is set equal to 100%.

EXAMPLE 8
Data Analysis (Normalization)

The method of the present invention measures total antioxidant function. Using lymphocytes stimulated to grow by a mitogen, antioxidant function was expressed by measuring growth response of lymphocytes with and without several doses of CuOOH. The CuOOH was the oxidative stress used to test the antioxidant function of lymphocytes from each individual. The initial reference range was established. However, since CuOOH by its nature is unstable, it has a relatively short shelf life, and its activity decays with time. Therefore, a different potency when first manufactured must be used periodically. Each batch was acquired at different times in its shelf life and it was required to fit each daily run to the original reference range values. The doses of CuOOH used (100 $\mu$M, 200 $\mu$M, 300 $\mu$M, 400 $\mu$M) were established with the original lot number of CuOOH in 1993/1994.

This normalization of values was performed on each daily batch of samples. A four-point dose-response curve for CuOOH was performed for each test, therefore one can fit the data for each daily batch to the original reference range, and use the new values to report the test. The normalization was accomplished by finding the average, median, range and variance of each CuOOH dose for each day. The value(s) closest to the original reference range (which is at 50% control growth), were compared statistically by t-test. The CuOOH dose most closely matching the reference range was then used for the Test result. Also, values halfway between CuOOH doses (such as 200+300/2) may be used. Normalization was accomplished by using Microsoft Excel Spreadsheet program.

EXAMPLE 9
Overview

For each daily batch number of patient samples, normalization was performed. Statistical analysis was performed to determine the mean, median, range, and variance of each CuOOH dose using the Descriptive Statistics function in Excel. Doses closest to the reference range were selected, and a t-test was performed by Excel to determine if the CuOOH dose was different or the same as the reference range. The dose with the two-tailed P value closest to 1.0 (and greater than 0.05) was used for reporting the values. The results were printed out, and kept with the folder for the batch.

EXAMPLE 10
Equipment, Reagents and Solutions

The following equipment was used in the assay of the present invention: Laminar Flow Hood, Centrifuge, Beckman GS-6, Cell Counter (Coulter Model T540), 12 Channel Pipettor (5–500 $\mu$l), Electric Pipet Pump (Drummond), Sterile 50 ml conical plastic tubes with caps, 12×75 mm polypropylene tubes, Sterile 15 ml conical plastic centrifuge tubes with caps, Pipettors (0–20, 0–200, 0–100 $\mu$l ranges), Sterile Glass Disposable Pipettes—5.0 ml, 10.0 ml, Test Tube Racks and Aerosol Barrier Pipet Tips (0–50 $\mu$l). TABLE II shows the various reagents and their sources used in the method of the present invention.

TABLE II

| Reagents | | |
|---|---|---|
| Adenine Hydrochloride | Sigma | A 8751 |
| Antibiotic Solution (PSF) | GIBCO | 15245-012 |
| Arginine Hydrochloride | Sigma | A 5131 |
| d-Biotin | Sigma | B 4501 |
| Calcium Chloride, Anhydrous | Sigma | C 4991 |
| Choline Chloride | Sigma | C 1879 |
| Cumene Hydroperoxide | Sigma | C 0524 |
| Cyanocobalamin (Vitamin $B_{12}$) | Sigma | V 2876 |
| Cystein Hydrochloride, Anhyd. | Sigma | C 1276 |
| Disodium EDTA | Sigma | E 4884 |
| Ferrous Sulfate Heptahydrate | Sigma | F 8633 |
| Folinic Acid, Calcium Salt | Sigma | F 7878 |
| Glucose | Sigma | G 5767 |
| Glucose Solution (10%) | Sigma | G 3126 |
| L-Glutamine | Sigma | G 3126 |
| Glycine | Sigma | G 7126 |
| HEPES, Free Acid | Sigma | H 3375 |
| L-Histidine (HCL monohydrate | Sigma | H 8125 |
| Histopaque (Ficoll/Diatrizoate) | Sigma | 1077-1 |
| Hydroxocobalamin (HCI ($B_{12}$) | Sigma | H 7126 |
| myo-Inositol | Sigma | I 5125 |
| L-Isoleucine | Sigma | I 2752 |
| L-Leucine | Sigma | L 8000 |
| L-Lysine | Sigma | L 5626 |
| Magnesium Sulfate, Anhydrous | Sigma | M 7506 |
| Methanol, Absolute | VWR | VWR4300-7 |
| L-Methionine | Sigma | M 9625 |
| Niacinamide (Vitamin $B_3$) | Sigma | N 3376 |
| D-Pantothenate, Calcium | Sigma | P 0290 |
| Phenol Red Solution, 0.5% PBS | Sigma | P 0290 |
| L-Phenylalanine | Sigma | P 2126 |
| Phosphate-Buffered Saline pH 7.4 | Sigma | P 3813 |

TABLE II-continued

| Reagents | | |
|---|---|---|
| Phytohemagglutinin PHA-P | Sigma | L 8754 |
| Potassium Phosphate, Dibasic | Sigma | P 3786 |
| Pyridoxine (HCl (Vitamin $B_6$) | Sigma | P 9755 |
| Riboflavin (Vitamin $B_2$) | Sigma | R 4500 |
| L-Serine | Sigma | S 4500 |

TABLE II-continued

| Reagents | | |
|---|---|---|
| Sodium Chloride | Sigma | S 9625 |
| Sodium Hydroxide, 5.0N Solution | VWR | RS 4151 |
| Sodium Pyruvate | Sigma | P 2256 |
| Sodium Pyruvate Sol. (100 mM) | Sigma | S 8636 |
| Thiamin (Vitamin $B_1$) | Sigma | T 4625 |
| L-Threonine | Sigma | T 8625 |
| Thymidine | Sigma | T 9250 |
| [$^3$H] - Thymidine | ICN | 24066 |
| L-Tryptophan | Sigma | T 0254 |
| L-Tyrosine | Sigma | T 3754 |
| L-Valine | Sigma | V 0500 |

EXAMPLE 11
Solutions

All solutions were prepared using tissue culture grade deionized water (tcd $H_2O$). To prepare a phosphate buffered saline (PBS)+0.72% Glucose (PBS-G) solution, PBS was prepared according to package instructions using tcd $H_2O$. Sufficient 10% glucose solution was added to achieve final glucose concentration of 0.72%. The solution was sterilized by filtration and stored in a refrigerator at (2–8° C.).

To prepare a concentrated (2×) stock media, (one) liter of (2×) stock media contains: (1) 23.80 g HEPES; (2) 14.02 g Sodium Chloride; (3) 1.05 g Dibasic Potassium Phosphate; (4) 0.241 g Magnesium Sulfate; (5) 1.0 ml (10 µM) Adenine Hydrochloride; (6) 30.0 ml (100 mM) Sodium Pyruvate; (7) 0.5 ml 0.5% Phenol Red; (8) 5.0 ml Antibiotic Mixture; (9) 8.0 ml 5N Sodium Hydroxide; (10) 20.0 ml Fe/EDTA (1.0 mM $FeSO_4$/0.4 mM $Na_2EDTA$). After all materials have been thoroughly mixed, pH was adjusted to 7.60 using 5N Sodium Hydroxide. A final volume of 1.0 L was achieved with tcd $H_2O$. The solution was sterilized by filtration through a 0.2 µM filter and stored in a refrigerator at 4° C. Under these circumstances, the stability was about 4 weeks.

The Basal Media used for 100% plate control and the novel method of the present invention was as follows. One should use a sterile technique after filtration. The Basal Media was prepared under laminar flow hoods. All ingredients mixed and brought to the final desired volume with tcd $H_2O$. The solution was sterilized by vacuum filtration into sterile bottles. The proper volume of PHA Stock Solution was added.

TABLE III

| | FINAL VOLUME BASAL MEDIA (ML) | | | | | |
|---|---|---|---|---|---|---|
| STOCK SOLUTION | 100 ml | 250 ml | 500 ml | 1000 ml | 1500 ml | 2000 ml |
| 2× Stock Media (ml) | 50 | 125 | 250 | 500 | 750 | 1000 |
| Thiamin ($B_1$) Stock (µl) | 10 | 25 | 50 | 100 | 150 | 200 |
| Riboflavin ($B_2$) Stock (µl) | 10 | 25 | 50 | 100 | 150 | 200 |
| Niacinamide ($B_3$) Stock (µl) | 10 | 25 | 50 | 100 | 150 | 200 |
| Pyridoxine ($B_6$) Stock (µl) | 10 | 25 | 50 | 100 | 150 | 200 |
| Vitamin B12 Stock (µl) | 10 | 25 | 50 | 100 | 150 | 200 |
| 2nd Stock Folinic (µl) | 10 | 25 | 50 | 100 | 150 | 200 |
| Pantothenate Stock (µl) | 10 | 25 | 50 | 100 | 150 | 200 |
| Biotin Stock (µl) | 10 | 25 | 50 | 100 | 150 | 200 |
| Stock Glucose (ml) | 0.72 | 1.8 | 3.6 | 7.2 | 10.8 | 14.4 |
| Stock Chol/Ino (ml) | 1.0 | 2.5 | 5.0 | 10.0 | 15.0 | 20.0 |
| Stock All Aminos (ml) | 1.0 | 2.5 | 5.0 | 10.0 | 15.0 | 20.0 |
| Stock $CaCl_2$(ml) | 0.5 | 1.25 | 2.5 | 5.0 | 7.5 | 10.0 |
| PHA (ml) | 0.2 | 0.5 | 1.0 | 2.0 | 3.0 | 4.0 |

EXAMPLE 12
Cumene Hydroperoxide (CuOOH) Stock Solutions

Cumene hydroperoxide (Sigma C 0524) has a limited shelf life. Expiration date of the material is three (3) months from date of receipt from Sigma. When pipetting CuOOH from the bottle, one should be aware of the increased viscosity of CuOOH. One must ensure that aspiration of liquid into the pipet tip is complete. This requires extra time and attention to ensure adequate fill of pipet tip. Also, one must wipe the tip to remove excess CuOOH on the outside of the pipet tip. Likewise, one must dispense the CuOOH completely. Following this procedure, one may store the solution under refrigerated conditions (2–8° C.) with desirable stability for 3 months.

For the first CuOOH stock solution (1.0 M CuOOH in PBS-G), 9.5 µl cumene hydroperoxide (CuOOH) are mixed with 990.5 µl PBS-G. Following this procedure, one may store the solution under refrigerated conditions (2–8° C.) with desirable stability for 3 months.

The second CuOOH stock solution (100 mM in PBS-G) must be prepared daily before cell isolation. It should not be stored overnight. To prepare the second CuOOH stock solution, 200 µl of the first stock solution were mixed with 1800 µl of PBS-G.

For the cumene hydroperoxide working solutions, 4 working solutions were prepared daily before cell isolation. The solution was added to the CuOOH Transfer Plate (separate microtiter plate) for loading of patient plates. The solutions should not be stored overnight. The 4 working solutions were:

(1) 100 µM CuOOH: 110 µl of the second CuOOH Stock was mixed with 4890 µl PBS-G;

(2) 200 µM CuOOH: 220 µl of the second CuOOH Stock was mixed with 4780 µl PBS-G;

(3) 300 µM CuOOH: 330 µl of the second CuOOH Stock was mixed with 4670 µl PBS-G; and (4) 400 µM CuOOH: 440 µl of the second CuOOH Stock was mixed with 4560 µl PBS-G.

EXAMPLE 13

Thymidine (ThY) Stock Solution

The thymidine (ThY) stock solution (cold): (1.33 mM ThY, 0.322 g/L) was prepared as follows: 0.161 g ThY (Sigma T 9250) were weighed and dissolved in tcd $H_2O$ to final volume of 500 ml. The solution was sterilized by vacuum filtration into a sterile bottle, using aseptic technique. The solution was aliquoted into 50 ml centrifuge tubes. For short-term storage, the solution can be refrigerated (4° C.) with stability for one month. For long-term storage, the solution can be refrigerated (−70° C.) with stability for 6 months. The thymidine working solution should be used to dilute radioactive thymidine ($H^3TdR$) for labeling of cells.

To prepare the thymidine working solution (ThY+$^3$H-TdR), to 300 ml sterile, de-gassed tcd $H_2O$ were added the following: 1.15 ml of 1.33 mM ThY (Cold), 1.70 ml of $^3$H-TdR (ICN part #24066), and 300 $\mu$Ci/mmol specific activity. Following this procedure, one may store the solution under refrigerated conditions (4° C.) with desirable stability for 1 week.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A cell culture medium effective for determining nutritional deficiencies, inadequacies, and imbalances of human lymphocytes and to biochemically analyze antioxidant functions of human lymphocytes, said medium comprising:

a buffered, serum-free stock solution containing the following ingredients:

a carbohydrate selected from the group consisting of glucose and a carbohydrate that produces glucose in the lymphocytes, a biologically usable form of pantothenic acid, choline or a biological usable form of a substance that produces choline in the lymphocytes, inorganic ions comprising chloride, phosphate, calcium, magnesium, potassium, sodium, and iron in a biologically utilizable form, cumene hydroperoxide, deionized water, and a mitogen to stimulate the growth of lymphocytes being assayed;

said buffered, serum-free stock solution having a pH from about 6.8 to 7.6, whereby the ingredients in said cell culture medium are present in amounts effective to determine nutritional deficiencies, inadequacies, and imbalances of the lymphocytes and to biochemically analyze antioxidant functions of the lymphocytes when said culture medium is supplemented with a nutrient supplement selected from the group consisting of biological utilizable forms of amino acids and vitamins, wherein a nutrient being tested for is omitted from or is present in limiting or inhibitory amounts in the nutrient supplement.

2. The cell culture medium of claim 1, wherein said vitamins are selected from the group consisting of biotin, folinic acid, a biologically usable form of folic acid, nicotinamide, nicotinic acid, riboflavin, thiamin, vitamin $B_6$, vitamin $B_{12}$, and compounds that produce them in the lymphocytes; and wherein said amino acids comprise L-arginine, L-cysteine, L-glutamine, glycine, L-histidine, L-isoleucine, L-leucine, L-lysine, L-methionine, L-phenylalanine, L-serine, L-threonine, L-tryptophan, L-tyrosine, L-valine, and compounds that produce said named amino acids, wherein the amino acids are present as a group.

3. The cell cuture medium of claim 1, wherein said cumene hydroperoxide is present in a concentration of from about 50 $\mu$M to about 500 $\mu$M.

4. The cell culture medium of claim 1, wherein the cell culture medium is supplemented at concentrations eliciting approximately a maximal growth response of the lymphocytes with one or more stimulatory nutrients selected from the group consisting of pyruvate, adenine, and inositol or compounds that produce them within the cells.

5. The cell culture medium of claim 2, wherein each amino acid is present in about a minimum concentration effective for a maximal growth response of the lymphocytes except an amino acid being tested, wherein said amino acid being tested is omitted or present in a concentration less than said minimum concentration effective for said maximal growth response.

6. The cell culture medium of claim 2, wherein the medium is free of either or both serine and glycine, and in which an effective concentration for lymphocyte growth response of either or both vitamin $B_6$ and a utilizable form of folic acid are included in the culture medium.

7. The cell culture medium of claim 2, wherein the medium is free of one of pantothenic acid and choline, the cell culture medium being effective to determine nutritional deficiencies and abnormal requirements of lymphocytes when supplemented with response-limiting amounts of pantothenic acid and choline.

* * * * *

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In the Abstract, line 3, "comprising, a buffered," should read --comprising a buffered,--.

In the Abstract, line 20, "steps of: inoculating" should read --steps of inoculating--.

In the Abstract, line 23, "medium; and" should read --medium and--.

In Figure 1, please add the title as follows --Essential Metabolics Analysis Antioxidant Function Test--.

In Column 1, line 37, please delete the comma after "radicals".

In Column 1, line 40, please insert the word --and-- between the words "catalase," and "glutathione".

In Column 2, line 13, please delete the comma after the word "comprising".

In Column 2, line 16, "cells, a" should read --cells; a--.

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In Column 2, line 19, "cells, inorganic" should read --cells; inorganic--.

In Column 2, line 21, "form, cumene" should read --form; cumene--.

In Column 2, line 23, "assayed; said" should read --assayed, said--.

In Column 2, line 31, please delete the colon after the word "of".

In Column 2, lines 44-45, please remove the paragraph indention so that it reads --medium; and comparing--.

In Column 3, line 1, "DRAWINGS" should read --DRAWING--.

In Column 3, line 8, "drawings" should read --drawing--.

In Column 3, line 8, "These drawings form" should read --This drawing forms--.

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In Column 3, line 10, "drawings illustrate" should read --drawing illustrates--.

In Column 4, line 29, "Allowance" should read --Allowances--.

In Column 4, line 46, "fatique" should read --fatigue--.

In Column 4, line 59, please remove the comma after the word "comprising".

In Column 6, line 25, "that's" should read --that is--.

In Column 6, line 37, "on Accession" should read --an accession--.

In Column 6, line 44, "(2) two" should read --2--.

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In Column 6, line 60, "is" should read --was--.

In Column 7, line 25, "is" should read --was--.

In Column 7, line 28, please insert a comma after "THSD/mm$^3$".

In Column 7, line 30, please insert a comma after "THSD/mm$^3$".

In Column 8, line 48, "was" should read --were--.

In Column 8, line 58, "wer" should read --were--.

In Column 8, line 61, "was" should read --were--.

In Column 9, line 27, please insert the word --were-- before the word "loaded".

In Column 9, line 29, please insert a comma after the word "pressed".

In Column 10, in line 18 under the heading of Table 2, "(HCL monohydrate" should read --(HCL monohydrate)--.

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In Column 10, in line 20 under the heading of Table 2, "(HCI $(B_{12})$" should read --(HCI $(B_{12})$)--.

In Column 11, in line 3 under the heading of Table 2, "(HCI (Vitamin $B_6$)" should read --(HCI (Vitamin $B_6$))--.

In Column 11, in line 10 under the heading Table 2, "(Vitamin $B_1$)" should read --(Vitamin $B_1$)--.

In Column 11, line 54, "(2-8° C.)." should read --2-8° C.--.

In Column 12, line 13 under the heading Table 3, containing the following "Stock $CaCl_2$(ml)", should be underlined.

UNITED STATES PATENT AND TRADEMARK OFFICE
CERTIFICATE OF CORRECTION

PATENT NO. : 5,985,665
DATED : November 16, 1999
INVENTOR(S) : J. Fred Crawford, et al It is certified that error appears in the above-identified patent and that said Letters Patent is hereby corrected as shown below:

In Column 12, line 33, "three (3)" should read --3--.

Signed and Sealed this

Twenty-fourth Day of April, 2001

*Attest:*

NICHOLAS P. GODICI

*Attesting Officer*    *Acting Director of the United States Patent and Trademark Office*